(12) United States Patent
Perkins

(10) Patent No.: US 12,667,373 B2
(45) Date of Patent: Jun. 30, 2026

(54) SAFETY HIP FEMORAL BONE PREPARATION INSTRUMENTS FOR THE FEMUR IN MINIMALLY INVASIVE TOTAL HIP ARTHROPLASTY

(71) Applicant: VEP Medical LLC, Henrico, VA (US)

(72) Inventor: James P. Perkins, Henrico, VA (US)

(73) Assignee: VEP Medical LLC, Henrico, VA (US)

( * ) Notice: Subject to any disclaimer, the term of this patent is extended or adjusted under 35 U.S.C. 154(b) by 0 days.

(21) Appl. No.: 17/827,207

(22) Filed: May 27, 2022

(65) Prior Publication Data

US 2023/0380846 A1    Nov. 30, 2023

(51) Int. Cl.
*A61B 17/16* (2006.01)
*A61F 2/36* (2006.01)
*A61F 2/46* (2006.01)

(52) U.S. Cl.
CPC ............ *A61B 17/1668* (2013.01); *A61F 2/36* (2013.01); *A61F 2/4607* (2013.01)

(58) Field of Classification Search
CPC .............. A61B 17/164; A61B 17/1659; A61B 17/1668; A61B 17/1684; A61F 2/36; A61F 2/4607; A61F 2/4612
See application file for complete search history.

(56) References Cited

U.S. PATENT DOCUMENTS

| | | | |
|---|---|---|---|
| 5,931,841 A | 8/1999 | Ralph | |
| 6,117,138 A | * 9/2000 | Burrows | ............... A61F 2/4684 606/86 R |
| 6,120,508 A | * 9/2000 | Grunig | ............... A61B 17/1659 606/85 |
| 8,211,183 B2 | 7/2012 | Podolsky | |
| 10,898,336 B2 | 1/2021 | Reubelt et al. | |

OTHER PUBLICATIONS

Waldemar Link GmbH & Co. KG, Link(R), TrabecuLink Femoral and Tibial Cones, Surgical Technique Catalog, 2020, 28 pages.

* cited by examiner

*Primary Examiner* — Brian A Dukert
(74) *Attorney, Agent, or Firm* — Lewis Rice LLC

(57) ABSTRACT

A safety broach for use in arthroplasty for hip joints, and a system including the same. The system may further include a segmented or otherwise flexible reamer and an implant. The safety broach includes a hollow interior passage that serves to guide the reamer when the safety broach is in place in the bone. The system may include any number of sizes of safety broaches, segmented reamers, and implants. In any case, such a safety broach may be capable of assisting with arthroplasty for hip joints (or any other joint), while typically providing enhanced safety and reliability of the arthroplasty.

18 Claims, 3 Drawing Sheets

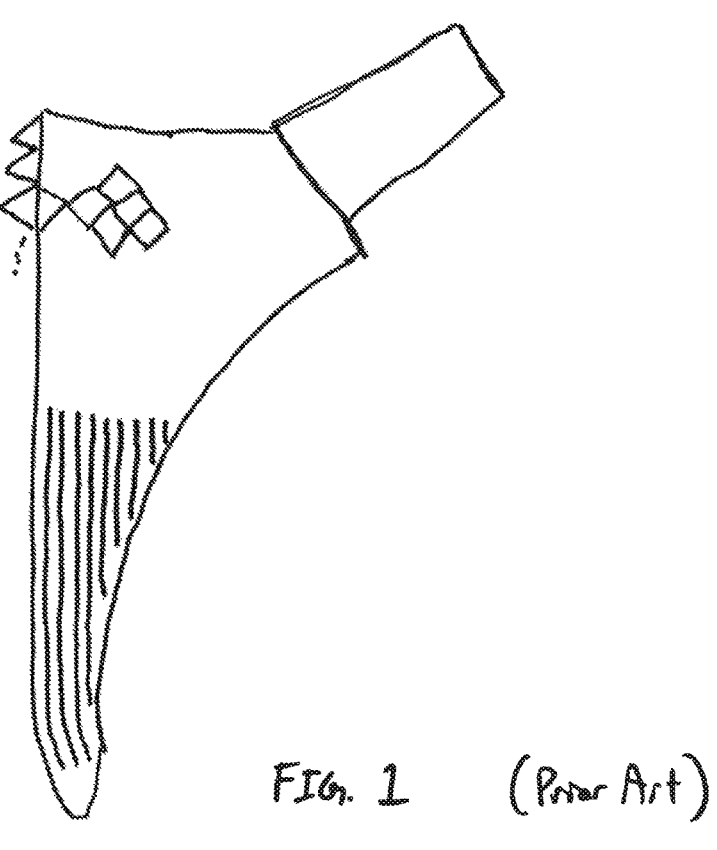
FIG. 1     (Prior Art)
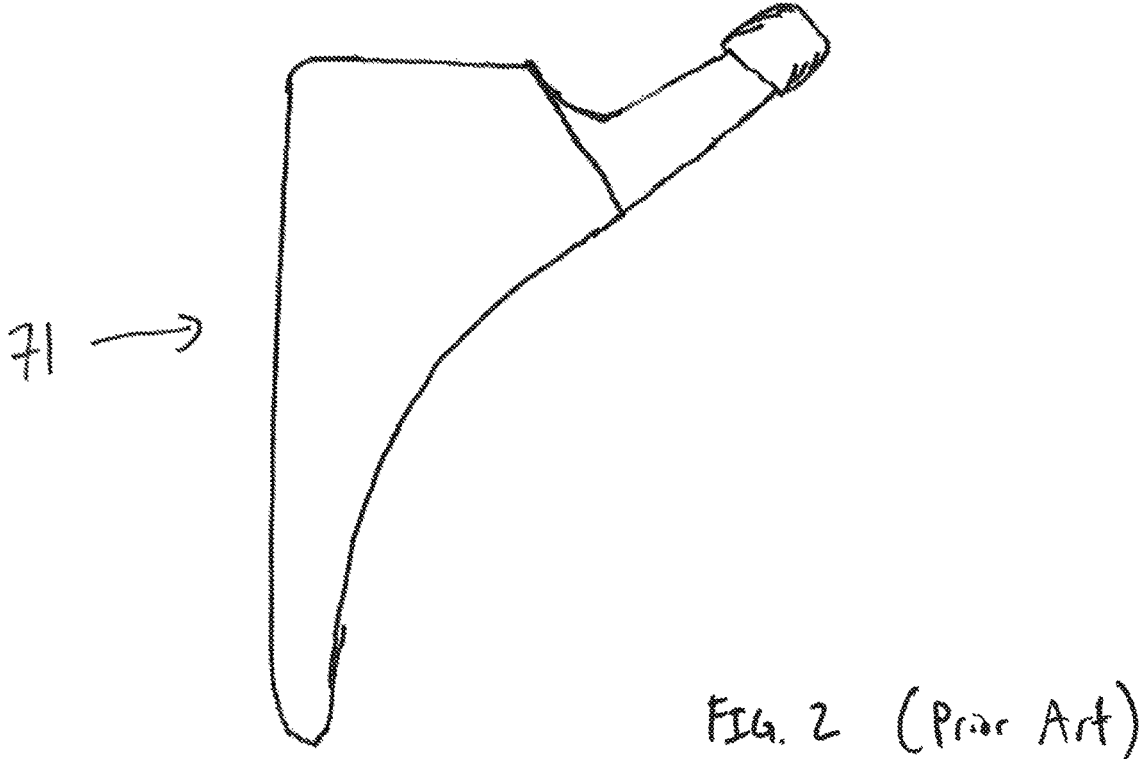
71 →
FIG. 2 (Prior Art)

SAFETY HIP FEMORAL BONE PREPARATION INSTRUMENTS FOR THE FEMUR IN MINIMALLY INVASIVE TOTAL HIP ARTHROPLASTY

BACKGROUND OF THE INVENTION

1. Field of the Invention

This disclosure is related to the field of joint replacement tools and instruments. More particularly to bone preparation instruments for minimally invasive total joint arthroplasty.

2. Description of the Related Art

Arthroplasty is a surgical procedure to restore the function of a joint. A joint can be restored by resurfacing the bones. An artificial joint (called a prosthesis) may also be used. Such artificial joints must be surgically implanted to be effective, which surgical procedures may carry many risks. Accordingly, arthroplasty is typically used when alternate medical treatments no longer effectively relieve joint pain and disability. People who have arthroplasty generally have substantial improvement in their joint pain, ability to perform activities, and quality of life. Most joint surgery involves the hip and knee, with surgery on the ankle, elbow, shoulder, and fingers being done less often.

Arthroplasty for the hip joint is well-known. For example, devices for preparing bone and other portions of some arthroplasty processes are described in U.S. Pat. Nos. 10,898,336, 8,211,183, and 5,931,841. Each disclosure from these U.S. patents is hereby incorporated herein by reference.

In some arthroplasty processes for hip replacements, a reamer may be used to hollow out portions of a bone, such as a femur, to make room and a snug fit for an orthopedic implant, such as a hip implant. The removal is necessary so that the implant may make solid contact with the bone to support the forces expected to be placed on that implant during its useful lifespan. A broach may be used to further shape the relevant cavity. As would be understood by persons of ordinary skill in the art, broaches are tools designed to shape and enlarge cavities in bone and/or to remove material from bone during surgical procedures. They are typically manual, handheld instruments with an elongated, tapered, and serrated working end and a handle. Such broaches are typically used in bone cavity preparation for implant insertion.

Broaches and reamers are often used because the can effectively shape a cavity within a bone to match that of a related implant. This is why many broaches tend to have a similar shape, much like the prior art broach shown in FIG. 1. Broaches are shaped to be the same shape and size as a related implant, much like the prior art implant shown in FIG. 2. The shape shown in FIGS. 1 and 2 is typical of many implants/broaches—wide proximate to the artificial joint and narrower towards the stem of the implant, which stem reaches furthest into the related bone. This shape takes advantage of the shape of large bones, such as those found in shoulders and hips, providing sufficient surface area to diffuse forces where anticipated over the lifespan of the implant. And again, because broaches are intended to remove small amounts of material at a time and tapped into place, they tend to be shaped like their related implants.

Broaches are seldom, if ever, the only tool used to form a cavity for an implant. Reamers are also extensively used. Reamers are often used before and during the use of a broach because reamers are capable of clearing out bone faster and in a fairly unconstrained manner. The downside to this is that reamers may remove too much bone unintentionally.

A prior process for removing bone using a broach and reamer to create a cavity in a bone for an implant will now be briefly described to illustrate some potential drawbacks to prior broach and reamer processes. First, a reamer or other free cutting tool is used to create an initial cavity. Once a sufficient cavity is present, a broach may be used to shape and enlarge the cavity. Typically, a set of broaches will be used, with each subsequent broach being slightly larger. In some cases, the area below the broach, the deepest portion of the cavity within the bone, will need to be lowered further into the bone. This may be done to provide some additional snugness to the broach by tapping it into the freshly reamed portion of the cavity, which tightness may be intended to provide the optimum cavity shape for the related implant.

However, this reaming process is unguided, both in a sense that the travel of the reamer though the bone cavity is unprotected and the cutting action of the reamer is not practically limited. This means that the reamer may cut and scrape the bone while being inserted into the cavity, while traveling to the bottom of the cavity, and while exiting the cavity. Further, and perhaps more concerning, the reamer is capable of cutting to a greater depth than intended or outside of the intended region in any direction. This may lead to problems with fitting an implant or even damaging the integrity of the hollowed bone's sidewall. Further, due to the constraints of working in situ within a person's body, the process of operating the reamer within the person may be difficult.

Accordingly, there is a need in the art for devices and systems that may increase the inherent safety of the arthroplasty processes for hip replacements. Missing in the art is a femoral bone preparation instruments for the femur in minimally invasive total hip arthroplasty that may benefit from advantages of both a broaching tool and a reaming tool, thereby improving the overall process, in at least some cases.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a bone preparation tool, the bone preparation tool comprising: a main body having two opposing ends and a hollow interior passage, wherein the main body also has a first opening at a first end and a second opening at a second end, the second end opposing the first end of the hollow interior passage; and a plurality of cutting features formed on the exterior surface of the main body.

In an embodiment of the bone preparation tool, the first opening is larger than the second opening.

In an embodiment of the bone preparation tool, the first opening is larger than the second opening.

In an embodiment of the bone preparation tool, the bone preparation tool further comprises a stem for manipulating the bone preparation tool.

In an embodiment of the bone preparation tool, the hollow body is configured to guide another bone preparation tool therethrough.

In an embodiment of the bone preparation tool, the bone preparation tool is sized and shaped to facilitate the shaping of a cavity in a human femur.

In an embodiment of the bone preparation tool, the human is an adult human.

In an embodiment of the bone preparation tool, the plurality of cutting features include teeth.

In an embodiment of the bone preparation tool, the plurality of cutting features further include ribs.

Also disclose herein is a hip replacement system, the system comprising: a first bone preparation tool comprising: a main body having two opposing ends and a hollow interior passage, wherein the main body also has a first opening at a first end and a second opening at a second end, the second end opposing the first end of the hollow interior passage; and a plurality of first cutting features formed on the exterior surface of the main body; wherein the hollow body is configured to guide a second bone preparation tool therethrough; the second bone preparation tool having a plurality of segments, at least one of the plurality of segments having a plurality of second cutting features; and an implant, wherein the implant, the first bone preparation tool, and the second bone preparation tool are each sized and shaped In an embodiment of the hip replacement system, the first bone preparation tool, the second bone preparation tool, and the implant are each configured to work together to create a portion of an artificial hip.

In an embodiment of the hip replacement system, the implant has a first implant portion and a second implant portion, wherein the first bone preparation tool is configured to shape a first cavity in a bone that is the same size and shape as the first implant portion, and wherein the second bone preparation tool is configured to shape a second cavity in a bone that is the same size and shape as the second implant portion.

In an embodiment of the hip replacement system, the first opening is larger than the second opening.

In an embodiment of the hip replacement system, the first opening is larger than the second opening.

In an embodiment of the hip replacement system, the hip replacement system further comprises a stem for manipulating the bone preparation tool.

In an embodiment of the hip replacement system, the hollow body is configured to guide another bone preparation tool therethrough.

In an embodiment of the hip replacement system, the bone preparation tool is sized and shaped to facilitate the shaping of a cavity in a human femur.

In an embodiment of the hip replacement system, the human is an adult human.

In an embodiment of the hip replacement system, the plurality of cutting features include teeth.

In an embodiment of the hip replacement system, the plurality of cutting features further include ribs.

BRIEF DESCRIPTION OF THE DRAWINGS

FIG. 1 depicts a prior art broach.

FIG. 2 depicts a prior art hip implant.

DETAILED DESCRIPTION OF THE PREFERRED EMBODIMENT(S)

This disclosure is focused on a safety broach for use in a system, the system further comprising a segmented reamer and a bone implant. This disclosure may also disclose methods of using the same. The system may be used to provide minimally invasive total hip arthroplasty (or other bone arthroplasty, such as shoulder arthroplasty). The safety broach may be configured to guide the segmented reamer, which guidance may improve safety and reduce errors.

Figure 3:
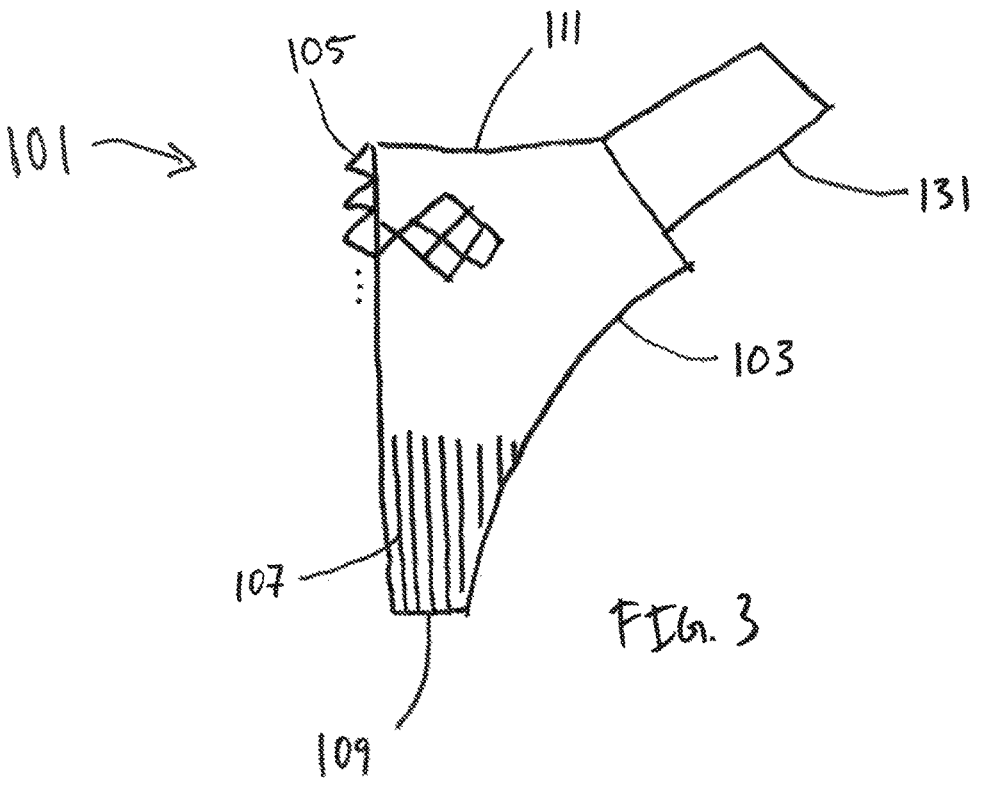
FIG. 3 depicts an embodiment of a safety broach in accordance with the instant application.
Figure 4:
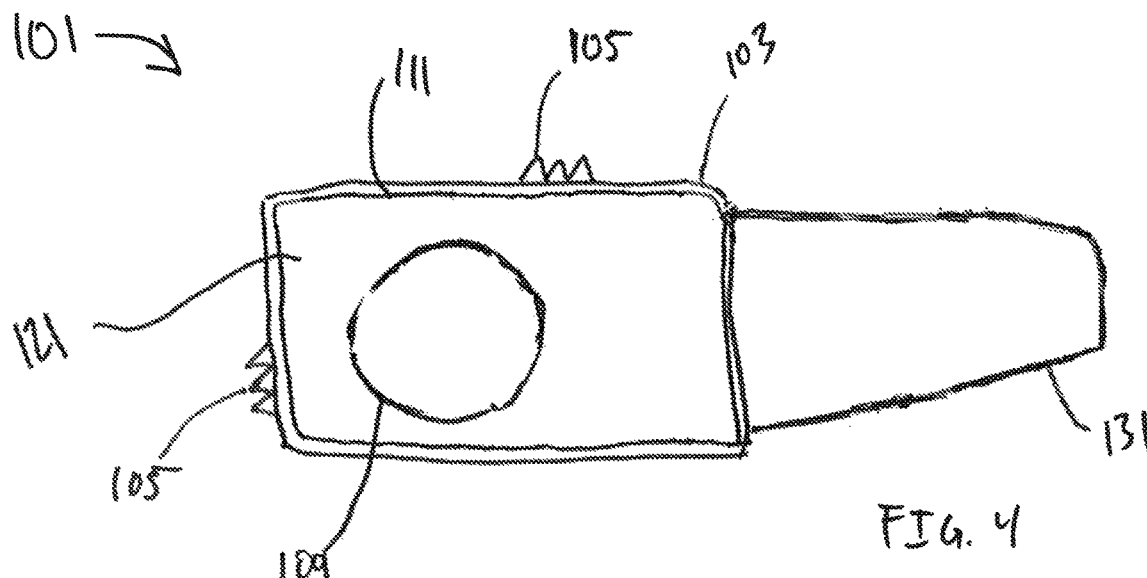
FIG. 4 depicts a top down view of the embodiment of a safety broach depicted in FIG. 3.
Figure 5:
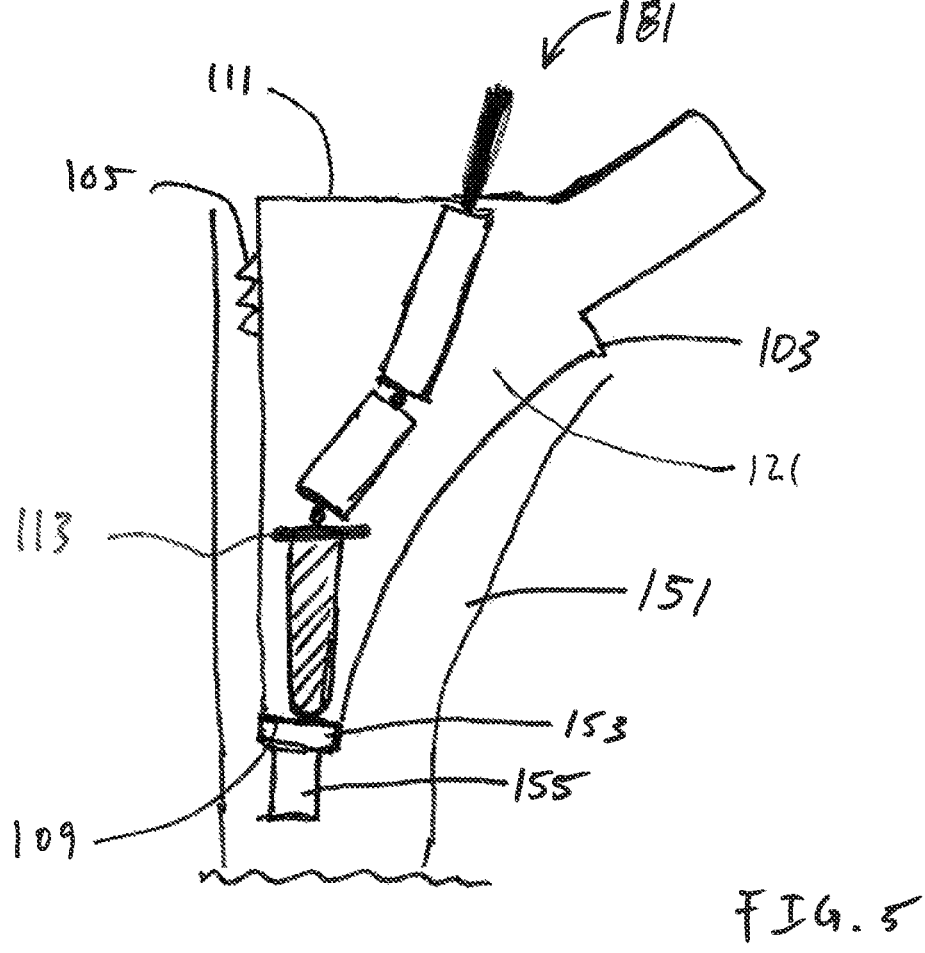
FIG. 5 depicts the safety broach of FIG. 3 within a bone and including a segmented reamer within the safety broach.

FIGS. 3, 4, and 5 herein illustrate embodiments of a safety broach (101). In the depicted embodiment, the safety broach (101) is intended to work with a bone implant (71), depicted in FIG. 2, and a segmented reamer (181). This embodiment of the safety broach (101) includes a main body (103) that typically has a shaped exterior surface that is at least partially covered with one or more cutting features (105, 107). The safety broach (101) may also include a stem (131) for use with various tools used during arthroplasty to manipulate a broach, as would be understood by persons of ordinary skill in the art. Such a stem (131) is optional, and any means for manipulating the safety broach (101) known to persons of ordinary skill in the art may be used.

The entire exterior surface of the main body (103) is typically covered in the one or more cutting features (105, 107). In the embodiment depicted in FIG. 3, the safety broach (101) has at least two types of cutting features (105, 107), including teeth (105) and ribs (107). In this disclosure, each cutting feature (105, 107) may be a single tooth, rib, or other structure. Thus, a number of cutting features (105, 107) may be of the same kind (for example, all teeth) or a mixture of different kinds (for example, at least one tooth and at least one rib). In other embodiments, any cutting feature or mixture of features (105, 107), in any total number, known to persons of ordinary skill in the art may be used. Typically, each cutting feature (105, 107) will be generally small, extending only slightly from the lower surface of the main body (103). Thus, the cutting features (105) depicted in FIGS. 3, 4 and 5 are generally exaggerated in their sizing for demonstrative purposes.

In the embodiment of a safety broach (101) shown in FIGS. 3, 4, and 5, the main body (103) includes a hollow passage through the interior of the main body (103), referred to herein as the hollow interior passage (121). The hollow interior passage (121) begins in a first opening (111) and ends in a second opening (109), each opening being formed in the main body's (103) exterior. The first opening (111) is almost always larger than the second opening (109), due at least to the preferred shape of broaches and implants. The hollow interior passage (121) may have any shape that tends to allow a related segmented reamer (181) to operate within the hollow interior passage (121). The hollow interior passage (121) will also be shaped to allow for the main body (103) to be sufficiently rigid to perform its role as a safety broach (101). In some embodiments, the hollow interior passage (121) may have a generally cylindrical shape. In other embodiments, the shape of the hollow interior passage (121) may start with a widest portion proximate to the first opening (111) that then tapers down to a narrower portion proximate to the second opening (109). In some embodiments, the hollow interior passage (121) may be configured to allow a segmented reamer (181) to safely move and articulate within the hollow interior passage (121) while also allowing the segmented reamer (181) to remove bone material from under the safety broach (101), which removal may facilitate the later acceptance of a stem of a related implant (71) to seat properly in the bone (typically a femur).

FIG. 3 depicts a side view of a safety broach (101) having a main body (103) and a stem (131). FIG. 4 depicts the safety broach (101) of FIG. 3 from a top down perspective, wherein the perspective allows much of the hollow interior passage (121) to be viewed through the first opening (111). As noted above, this figure makes clear that the first opening (111) is typically larger than the second opening (109). FIG. 5 depicts a cross-sectional side view of the safety broach (101) of FIG. 3, wherein the safety broach (101) is embedded into a femur (151). FIG. 5 also depicts a segmented reamer (181) within the hollow interior passage (121).

As shown in FIG. 5, the segmented reamer (181) may be inserted into the safety broach (101) while the safety broach (101) is within a bone (151) being processed. Further, the hollow interior passage (121) may guide the segmented reamer (181), preventing the segmented reamer (181) from contacting the bone (151) in locations other than those proximate to where desired. Instead, the interior hollow passage (121) may allow the segmented reamer (181) to contact the portion (153) of the bone (151) immediately below the second opening (109) in the main body (103). This may allow the segmented reamer (181) to remove a portion (155) of the bone (151) below the safety broach (101). This, in turn, may facilitate the insertion of the femoral stem of a hip implant (71) in the removed portion (155) of the bone (151).

FIG. 5 also depicts an embodiment of a segmented reamer (181). In this depicted embodiment, the segmented reamer (181) has three main segments, with a middle segment connected to each of the remaining segments via a flexible attachment. In some other embodiments, more or less segments may be used, or the segments may be substituted by any means that will provide flexibility. In some embodiments, the reamer (181) may be less flexible than the segmented reamer (181) depicted in FIG. 5. Typically, the end segment of the segmented reamer (181) will include cutting features so that the segmented reamer (181) may be used to shape a cavity in the relevant bone (151). For example, the cutting features may be used to remove the removed portion (155) of the bone (151), discussed above. Further, although the depicted segments are generally cylindrical, any shape may be used. In some embodiments, at least the cutting segment of the segmented reamer (181) is conical in shape, such that the distal end of the cutting segment is smaller in diameter than that of the portion proximate to the other segments. As used herein, cutting may include both removal by physical separation, removal by compacting material, or any other process known to persons of ordinary skill in the art that will result in the shaping of a cavity within a bone.

As shown in FIG. 5, the segmented reamer (181) may include a stop feature (113), which feature may provide additional safety benefits. In particular, the stop feature (113) may serve as an interfering portion of the segmented reamer (181), which interfering portion may limit the depth to which the segmented reamer (181) may travel, thereby limiting the material that may be removed (intentionally or unintentionally) by the segmented reamer (181). The interferences may be any kind of interference, wherein some portion of the segmented reamer (181) is physically constrained from cutting further.

For example, in the embodiment depicted in FIG. 5, the segmented reamer (181) will not be able to extend further into the main body (103) than where the stop feature (113) contacts the hollow interior passage (121) at or around the second opening (109). Here, the stop feature (113) may be a plate of material, or its equivalent, that is larger in diameter than the second opening (109). This difference in size means that the stop feature (113) may not travel through the second opening (109), much like a properly designed manhole cover is incapable of falling into its related manhole. In other embodiments, the stop feature (113) may interfere with other objects, thereby preventing over travel of the cutting features of the segmented reamer (181). In yet other embodiments, any form of interference may be used. For example, where the segmented reamer has a conical or otherwise expanding cutting portion, the second opening (109) may be smaller than the diameter of a portion of the conical or otherwise expanding cutting portion, such that larger section of the conical or otherwise expanding cutting portion may function as the interfering stop feature (113).

In other embodiments, the safety broach (101) may have any size or shape, and may be formed of any mixture of materials in any number of segments. In some embodiments, multiple safety broaches (101) may be used during a given arthroplasty procedure, with each safety broach (101) being slightly different sized, so that the related cavity in the relevant bone (151) (often a femur) may be slowly increased in size to the desired size.

Similarly, the system including the safety broach (101) may have various sizes of implants (71) and segmented reamers (181) so that the entire system can be coordinated as the size of the related cavity in the relevant bone (151) may be increased as a system. The end result typically is a superior fit for the hip implant (71). In some embodiments, the implant may be for a joint other than a hip.

In such a system, the segmented reamer (181), or other bone material removal tool, may be used to create an initial cavity in the bone (151) being shaped for the insertion of an implant (71). After the initial cavity is formed, the safety broach (101) may be used to enlarge and shape the initial cavity. The cutting features (105, 107) may work to shape the cavity by removing portions of bone or by compacting portions of bone. Larger and larger safety broaches (101) may be used to further enlarge the cavity in the bone (151). Then, the segmented reamer (181) may be inserted into the safety broach (101) via the first opening (111). The segmented reamer (181) may be guided all the way to the second opening (109), where the segmented reamer may be guided into contact with the bone (151) in the vicinity of the portion (153) of the bone (151) immediately below the second opening (109) in the main body (103).

The safety broach (101) may then facilitate the user in safely removing the removed portion (155) of the bone (151) at a region below the safety broach (101). As discussed above, this removed portion (155) may facilitate the insertion and fitment of a femoral stem in a related hip implant (71). After the process for removing the removed portion (155), the segmented reamer (181) may be removed from the safety broach (101) via the first opening (111) in the main body (101). Then, the safety broach (101) may be tapped further into the cavity, or the implant (71) may be inserted.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

Finally, the qualifier "generally," and similar qualifiers as used in the present case, would be understood by one of ordinary skill in the art to accommodate recognizable attempts to conform a device to the qualified term, which may nevertheless fall short of doing so. This is because terms such as "cylindrical" are purely geometric constructs and no real-world component is a truly "cylindrical" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A joint replacement system comprising:
a first bone preparation tool comprising:
   a first main body having two opposing ends and a hollow interior passage, wherein the main body also has a first opening at a first end and a second opening at a second end, the second opening opposing the first opening of the first main body; and
   a plurality of first cutting features formed on the exterior surface of the first main body; and
a second bone preparation tool comprising:
   a second main body having a plurality of cutting features and a plurality of segments,
wherein the hollow interior passage is configured for guiding the second bone preparation tool from the first end to the second end of the first main body, and
wherein the hollow interior passage is configured to allow the second bone preparation tool to exit the second end of the first main body, and
wherein the first bone preparation tool and the second bone preparation tool are configured to be used together.

2. The joint replacement system of claim 1, wherein the plurality of segments includes at least three segments.

3. The joint replacement system of claim 1, further comprising a flexible attachment made between two segments of the plurality of segments.

4. The joint replacement system of claim 1, wherein at least one segment of the plurality of segments is substantially cylindrical in shape.

5. The joint replacement system of claim 4, wherein each segment of the plurality of segments is substantially cylindrical in shape.

6. The joint replacement system of claim 1, wherein the second bone preparation tool further comprises a stop feature, the stop feature being configured to interfere with the second opening when the second bone preparation tool is inserted through the first opening and extends at least partially through the second opening.

7. The joint replacement system of claim 1, wherein the second bone preparation tool further comprises a stop feature, the stop feature being configured to limit the depth that the second bone preparation tool is capable of extending through the second opening.

8. The joint replacement system of claim 6, wherein the stop feature is provided at an end of a segment of the second bone preparation tool.

9. The joint replacement system of claim 7, wherein the stop feature is provided at an end of a segment of the second bone preparation tool.

10. The joint replacement system of claim 6, wherein the stop feature is a plate that has at least one dimension that is greater than at least one dimension of the second opening.

11. The joint replacement system of claim 7, wherein the stop feature is a plate that has at least one dimension that is greater than at least one dimension of the second opening.

12. The joint replacement system of claim 7, wherein the second bone preparation tool is a reamer.

13. The joint replacement system of claim 1, further comprising an implant, wherein the implant, first bone preparation tool, and the second bone preparation tool are configured to be used together.

14. The joint replacement system of claim 13, wherein the implant has a first implant portion and a second implant portion, wherein the first bone preparation tool is configured to shape a first cavity in a bone that is the same size and shape as the first implant portion, and wherein the second bone preparation tool is configured to shape a second cavity in a bone that is the same size and shape as the second implant portion.

15. The joint replacement system of claim 13, wherein the implant is a portion of an artificial hip.

16. The joint replacement system of claim 1, wherein at least a portion of the second bone preparation tool is size and shaped to extend through the second opening.

17. A bone preparation tool comprising:
a main body having two opposing ends and a hollow interior passage, wherein the main body also has a first opening at a first end and a second opening at a second end, the second end opposing the first end of the hollow interior passage;
a stem portion formed on an exterior surface of the main body and being configured to facilitate manipulation of the main body; and
a plurality of cutting features formed on the exterior surface of the main body,
wherein the hollow interior passage is configured to guide a second bone preparation tool from the first end to the second end, and
wherein the hollow interior passage is configured to allow the second bone preparation tool to exit the second end at the second opening,
wherein the first opening is larger than the second opening.

18. The bone preparation tool of claim 17, wherein the stem portion is integrally formed with the main body.

* * * * *